United States Patent [19]

Hutten

[11] 4,234,084
[45] Nov. 18, 1980

[54] COMBINED DISPLAY PACKAGE AND ARTICLE STORAGE CASE

[75] Inventor: James E. Hutten, Mason, Ohio

[73] Assignee: American Thermometer Co., Inc., Dayton, Ohio

[21] Appl. No.: 36,573

[22] Filed: May 7, 1979

[51] Int. Cl.$^3$ .................. A61B 19/02; B65D 25/22; B65D 75/36; B65D 75/58

[52] U.S. Cl. .................. 206/306; 206/484; 206/620; 206/634

[58] Field of Search .............. 206/461, 460, 372, 373, 206/466, 306, 363, 484, 620, 634

[56] References Cited

U.S. PATENT DOCUMENTS

| | | | |
|---|---|---|---|
| 2,801,002 | 7/1957 | Volckening et al. | 206/466 |
| 3,047,139 | 7/1962 | Jacoff | 206/372 |
| 3,235,063 | 2/1966 | Jarund | 206/820 |
| 3,527,346 | 9/1970 | Chalpin | 206/461 |
| 3,847,280 | 11/1974 | Poncy | 206/306 |

Primary Examiner—William T. Dixson, Jr.
Attorney, Agent, or Firm—Jacox & Meckstroth

[57] ABSTRACT

A cardboard panel is printed with identifying and advertising information and carries an article confined between two flexible sheets of transparent plastics material. The sheets are heat-welded together to form a display case for the article and have outwardly projecting border portions which are adhesively bonded to the front face of the panel. A line of weakening is formed within the sheets between the case and the border portions to provide for separating the case from the panel and to provide a reusable storage and carrying case for the article.

11 Claims, 4 Drawing Figures

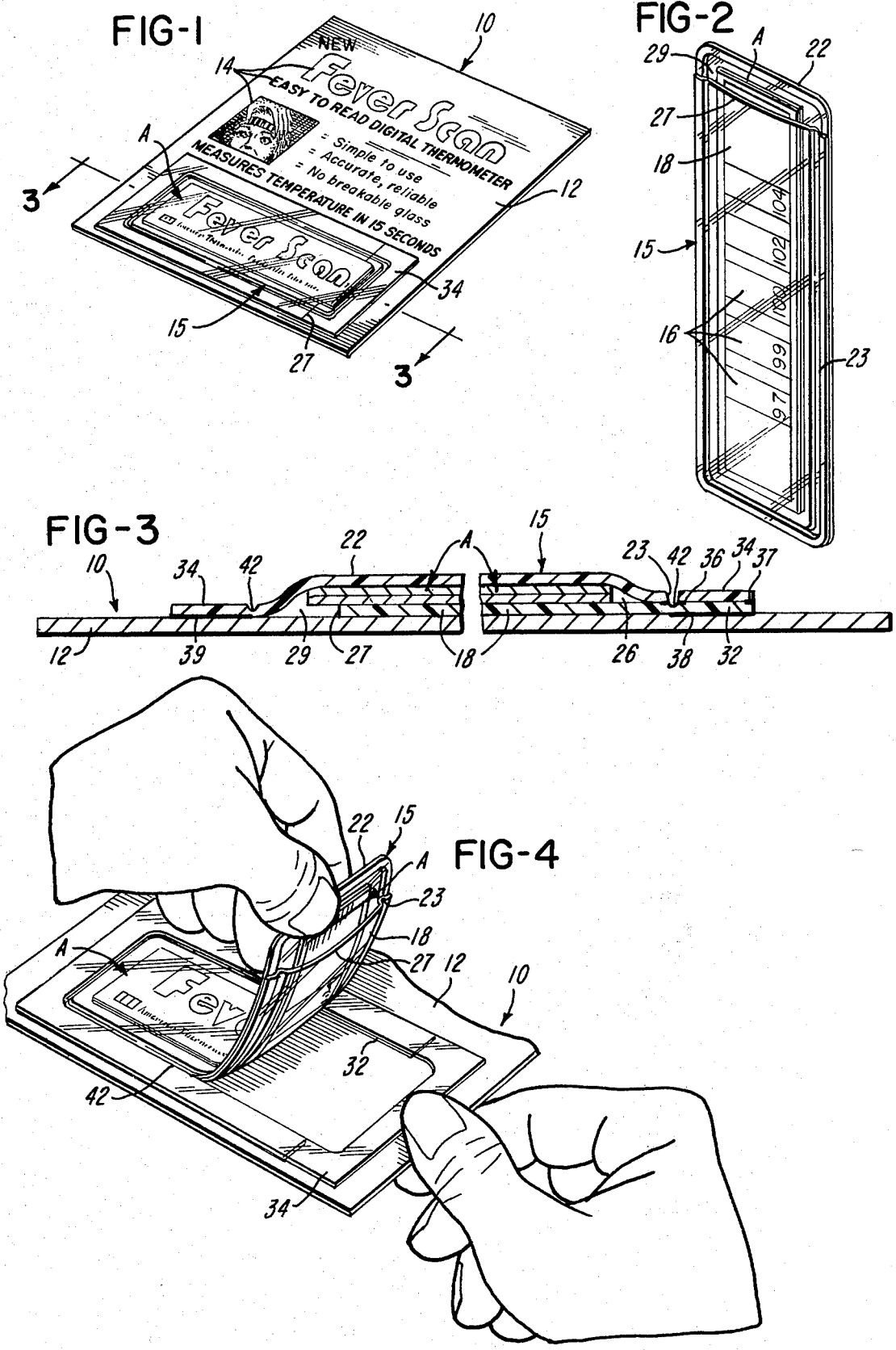

COMBINED DISPLAY PACKAGE AND ARTICLE STORAGE CASE

BACKGROUND OF THE INVENTION

In the art of packaging, it is common to attach an article to a printed cardboard sheet or panel by means of a transparent plastic bubble or blister which is heat-bonded to the panel. Usually the heat bond is formed by a heat activated clear adhesive coating which is applied to the panel. Various types of such packages are commonly referred to as a "blister pack", "skin pack" or "shrink pack", and the backing panel is commonly preprinted with the desired identifying and advertising data or information.

U.S. Pat. No. 3,341,006 discloses a bubble or blister package for an article which includes a reusable storage case. It has also been proposed to use the transparent plastic blister or bubble as a storage device for one or more articles. For example, the plastic bubble disclosed in U.S. Pat. No. 3,972,417 is used for storing double edge razor blades. U.S. Pat. No. 3,527,346 discloses another form of blister or bubble package wherein the transparent plastic bubble is used for covering and displaying an article carried by a cardboard panel. A portion of the panel is adapted to be folded into a base which receives the transparent bubble to form a rigid storage case for the article. Another form of reusable storage case or container is disclosed in U.S. Pat. No. 3,111,220. In this patent, the reusable transparent storage case is inserted into an aperture within the backing card or panel for transporting and display, but is removable from the aperture for use as a storage container.

SUMMARY OF THE INVENTION

The present invention is directed to the combination of an improved display package and storage case for an article and which provides a relatively inexpensive means for producing a reusable storage case and for attaching the case to a backing card or panel in a manner which enables the case to be quickly and conveniently separated from the panel.

In accordance with the illustrated embodiment of the invention, the above desirable features are provided by heat-welding together two sheets of flexible transparent plastics material to form a display envelope or case and a border portion which are separated by a line of weakening formed by scoring the welded sheets. An article is placed within the case and the border portions of the plastic sheets are bonded by heat activated adhesive to the front face of a cardboard backing panel which is preprinted with identifying and advertising information. After the package is purchased, the display case may be conveniently and quickly separated or peeled from the border portions along the line of weakening so that the display case becomes a reusable storage case for the article.

Other features and advantages of the invention will be apparent from the following description, the accompanying drawing and the appended claims.

BRIEF DESCRIPTION OF THE DRAWING

FIG. 1 is a perspective view of a combined display package and transparent article storing case constructed in accordance with the invention;

FIG. 2 is a perspective view of the transparent storage case and enclosed article after the case is separated from the display package shown in FIG. 1;

FIG. 3 is an enlarged cross-section of the combined display package and article storing case, as taken generally along the line 3—3 of FIG. 1; and FIG. 4 is another perspective view of a portion of the package shown in FIG. 1 and illustrating the manual separation of the reusable storage case from the package.

DESCRIPTION OF THE PREFERRED EMBODIMENT

FIG. 1 illustrates a shipping and display package 10 which includes a carrier or backing panel 12 preferably formed of cardboard. The panel 12 is printed with identifying and advertising data or information 14 such as, for example, information relating to a new digital thermometer and adjacent printed paper folder which together form an article A carried by the package 10. Preferably, the digital thermometer consists of a flexible strip of plastics material which carries a series of parallel spaced stripes 16 each formed by a coating of liquid crystals formulated to correspond to a predetermined temperature. The digital thermometer strip and adjacent paper folder are confined or enclosed within a rectangular case 15 which is formed by a first or inner sheet 18 and a second or outer sheet 22 of flexible transparent plastics material which may be heat welded together. In the illustrated embodiment, the sheets 18 and 22 are formed of polyvinylchloride.

As shown in FIG. 3, the plastic sheets 18 and 22 are heat-welded together along a U-shaped line 23 which extends along both sides of the case 15 and across one end to define a pocket 26 for enclosing the article A. The inner sheet 18 has an edge 27 which is spaced inwardly from the corresponding edge of the outer sheet 22 to define an opening 29 for inserting the article A into the pocket 26.

The case 15 forms part of the package 10 and is supported and carried by the backing panel 12 as a display case. In this form, the plastic sheets 18 and 22 include corresponding border portions 32 and 34 which extend around the case 15. The border portions 32 and 34 are secured together by U-shaped heat-weld lines 36 and 37 which extend along both sides and one end of the case 15. Thus in the embodiment illustrated, the border portion 34 of the outer sheet 22 extends completely around the case 15, and the border portion 32 of the sheet 18 extends around both sides and one end of the case 15 and terminates at the edge 27.

The backing panel 12 is coated with a layer of transparent adhesive which is activated in the area 38 by heat and pressure to bond the border portion 32 of the inner sheet 18 to the front face of the backing panel 12 around two sides and one end of the case 15. The border portion 34 of the outer sheet 22 projects on one end past the edge 27 of the sheet 18 and is bonded to the panel 12 in the area 39 by the heat activated adhesive. Since the frame-like border portion 34 and the U-shaped border portion 32 cooperate to extend completely around the case 15, the article A is enclosed and sealed within the pocket 26, and the case 15 is positively attached to the backing panel 12.

As best illustrated in FIG. 3, a line of weakening 42, in the form of a score line, extends within the sheets 18 and 22 between the case 15 and the outwardly projecting border portions 32 and 34. When it is desired to remove the case 15 from the backing panel 12, the score line 42 is completely ruptured or severed by peeling the case 15 from the surrounding frame-like border portions 32 and 34, as illustrated in FIG. 4. The case 15 may then be used for protecting, storing and transporting the article A.

From the drawing and the above description, it is apparent that a display package constructed in accordance with the present invention, provides desirable features and advantages. For example, the case 15 not only serves to display the article A within the case, but also may be conveniently and quickly separated from the backing panel 12 by simply peeling the case from the surrounding border portions. The attachment of the border portions 32 and 34 to the backing panel 12 also form a sealed protective enclosure for the article A. This deters pilferage since the article A cannot be removed from the package without at least partially separating the case 15 from the backing panel 12. The extension of the outer sheet 22 past the edge 27 of the inner sheet 18 to form the corresponding border portion 34 and the bonding of the border portion 34 to the backing panel 12 also provide a closure for the opening 29 to the pocket 26. Furthermore, the projection of the outer sheet 22 past the edge 27 of the inner sheet 18 provides for conveniently inserting and removing the article A from the case 15 after the case 15 is separated from the backing panel 12.

While the form of package herein described constitutes a preferred embodiment of the invention, it is to be understood that the invention is not limited to this precise package form, and that changes may be made therein without departing from the scope and spirit of the invention as defined in the appended claims.

The invention having thus been described, the following is claimed:

1. A package system adapted for shipping and displaying an article and for providing a reusable storage case for the article, comprising a backing panel of cardlike sheet material adapted to be printed, a first sheet of flexible material substantially smaller than said backing panel, a second sheet of flexible material substantially smaller than said backing panel, means connecting said first and second sheets to form a flexible case defining a pocket for receiving the article, at least one of said first and second sheets extending beyond said case and forming a border portion extending around said pocket, means for positively securing said border portion to said backing panel around said pocket, means defining a line of weakening extending around said pocket between said border portion and said means connecting said first and second sheets and providing for manually peeling said case from said border portion and said backing card after the package and article have been purchased, and means defining an opening within said case after said case is removed from said backing card to provide for conveniently removing and reinserting the article into said pocket.

2. A package system as defined in claim 1 wherein said border portion extends completely around the entire periphery of said case.

3. A package system as defined in claim 1 wherein said first and second sheets are each formed of a heat sealable plastics material, and said means connecting said first and second sheets comprise a heat weld.

4. A package system as defined in claim 3 wherein said first and second sheets comprise a polyvinyl chloride material.

5. A package system as defined in claim 1 wherein said means securing said border portion to said backing panel comprise a heat activated adhesive coating on said backing panel.

6. A package system as defined in claim 1 wherein said first and second sheets have corresponding border portions projecting from said case, and heat weld means securing said first and second sheets together within said border portions.

7. A package system as defined in claim 1 wherein the article comprises a flexible thermometer having liquid crystals for indicating temperature, and means for closing said opening until said case is separated from said border portion and said backing card.

8. A package system as defined in claim 1 wherein said border portion comprises a frame surrounding said case, said line of weakening extends completely around said case, and said frame is bonded to said backing panel.

9. A package system as defined in claim 1 wherein said backing panel comprises a cardboard panel, and a layer of heat activated adhesive bonding said border portion to said cardboard panel.

10. A package system as defined in claim 1 wherein said first sheet has an edge terminating inwardly of a corresponding overlying border portion of said second sheet, said edge cooperates with said second sheet to define said opening for said case, and said border portion of said second sheet is bonded to said card outwardly of said edge.

11. A package system adapted for shipping and displaying an article and for providing a reusable storage case for the article, comprising a cardboard backing panel adapted to be printed, a first sheet of flexible plastics material and a second sheet of flexible plastics material, heat weld lines connecting said first and second sheets to form a flexible case defining a pocket for receiving the article, a portion of said first and second sheets extending beyond said case and forming a frame-like border portion surrounding said case, means for securing said border portion to said backing panel, means defining a line of weakening extending around said case and between said border portion and said heat weld lines connecting said first and second sheets and providing for manually separating said case after said case is removed from said border portion after the package and article have been purchased, and means defining an opening within said case to provide for conveniently removing and reinserting the article into said pocket.

* * * * *